United States Patent [19]
Kim et al.

[11] Patent Number: 5,103,013
[45] Date of Patent: Apr. 7, 1992

[54] DITHIOKETENE DERIVATIVES, PHARMACEUTICAL COMPOSITIONS CONTAINING THE SAME AND USES THEREOF

[75] Inventors: Choong S. Kim; Jeong S. Chae; Ho Seong Yoo, all of Seoul; Jong W. Lee, Kyonggi; Jae G. Park; Jeong W. Lee, both of Seoul, all of Rep. of Korea

[73] Assignee: Yuhan Corporation, Ltd., Seoul, Rep. of Korea

[21] Appl. No.: 424,164

[22] Filed: Oct. 23, 1989

[30] Foreign Application Priority Data

Oct. 27, 1988 [KR] Rep. of Korea ............... 1988-14023

[51] Int. Cl.$^5$ ............... C07D 331/04; C07D 409/12; C07D 417/12
[52] U.S. Cl. .................... 548/195; 546/268; 546/284; 549/39; 549/89
[58] Field of Search ............... 549/39, 89; 548/195; 546/268, 284

[56] References Cited

U.S. PATENT DOCUMENTS

| | | | |
|---|---|---|---|
| 4,663,319 | 5/1987 | Iijima | 514/212 |
| 4,822,814 | 4/1989 | Ohyama | 514/440 |

FOREIGN PATENT DOCUMENTS

| | | | |
|---|---|---|---|
| 298040 | 1/1989 | European Pat. Off. | 549/39 |
| 2316921 | 4/1972 | Fed. Rep. of Germany | 549/39 |
| 2625220 | 4/1976 | Fed. Rep. of Germany | 549/39 |
| 49-39260 | 4/1974 | Japan | 549/39 |
| 49-101528 | 9/1974 | Japan | 549/39 |
| 62158274 | 10/1974 | Japan | 549/39 |
| 50-100062 | 8/1975 | Japan | 549/39 |
| 50-39666 | 12/1975 | Japan | 549/39 |
| 59-27887 | 2/1984 | Japan | 549/39 |

Primary Examiner—Robert Gerstl
Attorney, Agent, or Firm—Finnegan, Henderson, Farabow, Garrett & Dunner

[57] ABSTRACT

2-(1,3-Dithietan-2-ylidene)-2-[N-(subsittuted)carbamoyl]acetate esters and 2-(1,3-dithiolan-2-ylidene)-2-[N-(substituted) carbamoyl]acetate esters, having potent therapeutic and prophylactic effect for hepatic disorders, are provided.

4 Claims, No Drawings

DITHIOKETENE DERIVATIVES, PHARMACEUTICAL COMPOSITIONS CONTAINING THE SAME AND USES THEREOF

BACKGROUND OF THE INVENTION

1. Field of the Invention

The present invention relates to new dithioketene derivatives which exhibit excellent therapeutic and prophylactic effect for hepatic diseases and pharmaceutical compositions containing these compounds at a dose suitable for daily administration.

2. Description Of The Prior Art

Dialkyl 2-(1,3-dithietan-2-ylidene)malonates and the preparation thereof are disclosed in Ger. Offen. 2,625,220, 2,316,921 and Japan 74 39,260.

Dialkyl 2-(1,3-dithiolan-2-ylidene)malonates are disclosed in Japan Kokai 75 100,062, Japan 75 39,666 and 74 39,260.

Dithiolane derivatives, having a ketone functional group in the side chain, are disclosed in Japan Kokai Tokyo Koho JP 59 27,887.

Dithietane derivatives containing two ketone functional groups in the side chain are disclosed in Japan Kokai Tokyo Koho JP 62 158, 274 and Eur. Pat. Appl. EP 234,480.

Also, reference can be made in U.S. Ser. No. 206,659, which was filed by the same applicant of the present invention.

SUMMARY OF THE INVENTION

In brief, the present invention relates to compounds having less toxicity and improved pharmacological potency of the general formula (I)

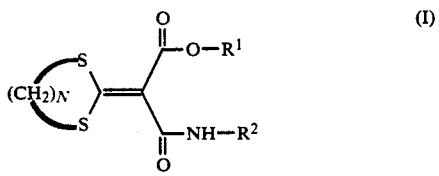

in which $R^1$ is a lower alkyl; $R^2$ is a hydrogen, lower alkyl, benzyl, phenyl, 4-hydroxyphenyl, halogenophenyl, 4-trifluoromethylphenyl, 2-thiazolyl, 4-methyl-2-thiazolyl, 4-phenyl-2-thiazolyl 2-pyridyl or 1,3,4-thiadiazol-2-yl; and n is 1 or 2.

Accordingly, it is an object of the present invention to provide novel dithioketene derivatives which possess excellent therapeutic and prophylactic effects for hepatic disorders.

Another object of the present invention is to provide pharmaceutical compositions containing said compounds at a dose suitable for daily administration.

DETAILED DESCRIPTION OF THE INVENTION

The present invention provides compounds of the general formula (I)

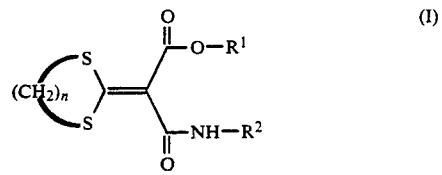

in which $R^1$ is a straight or branched alkyl group having 1 to 5 carbon atoms; $R^2$ is hydrogen, a straight or branched alkyl group having 1 to 5 carbon atoms, benzyl, phenyl, 4-hydroxyphenyl, halogenophenyl, 4-trifluoromethylphenyl, 2-thiazolyl, 4-methyl-2-thiazolyl, 4-phenyl-2-thiazolyl, 2-pyridyl or 1,3,4-thiadiazol-2-yl; and n is 1 or 2.

Two particularly preferred classes of formula I are formed when $R^1$ is methyl, ethyl, isopropyl or sec-butyl and n is 1 or 2. But in one class $R^2$ is hydrogen, a straight or branched alkyl group having 1 to 5 carbon atoms, and in the other class $R^2$ is phenyl, a substituted phenyl or a heteroaromatic ring.

The compounds according to the invention can be administered orally. They will, in general, be associated with a pharmaceutically acceptable carrier or diluent to provide a pharmaceutical dosage form.

The pharmaceutical composition can most conveniently be in the form of capsules or tablets, which may be in the form of slow releasing formulations. The composition may also take the form of a dragee or syrup.

The convenient daily dose would be of the order of 100 mg to 1.0 g per day and the form of dosage units contains from 50 mg to 200 mg.

The compounds of the present invention may be prepared from the reaction of an acid anhydride of formula (II) and an amine of formula (III);

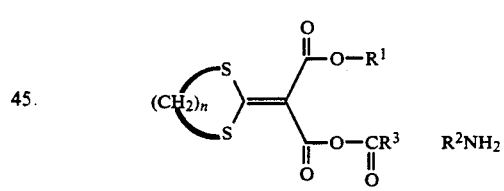

in which $R^1$, $R^2$ and n have the same meanings given previously and $R^3$ is tert-butyl, a lower alkoxy or benzyloxy.

The reaction may be carried out by allowing the acid anhydride (II) and the amine (III) to stand in a solvent such as methylene chloride, acetonitrile or alcohol. The reaction with a weakly basic heteroaromatic amine (e.g. 2-aminopyridine, 2-aminothiazole, or 2-amino-1,3,4-thiadiazole) can be carried out by heating the reaction mixture at 50°–100° C. in a solvent such as acetonitrile or N,N-dimethylformamide.

In an alternative procedure, the compounds of the present invention can be prepared from the reaction of an active ester of formula (IV) with an amine of formula (III);

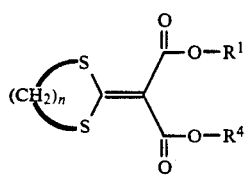 (IV)

wherein R¹ and n are the same as defined previously and R⁴ is 1-benzotriazolyl, N-succinimidoyl or N-phthalimidoyl.

The reaction can be carried out in a solvent such as acetonitrile, methylene chloride or N,N-dimethylformamide at 10°-100° C.

The reaction with alkyl amines or aniline derivatives can readily take place at a lower temperature (10°-30° C.), whereas the reaction with weakly basic heteroaromatic amines requires a high temperature (50°-100° C.).

In another process, the compounds of formula (I) can be prepared by reacting a monoacid of formula (V) with phosphorous pentachloride to yield an acid chloride of the monoacid which is very unstable. An amine of formula (III) is then added to the acid chloride of monoacid in the presence of pyridine or triethylamine,

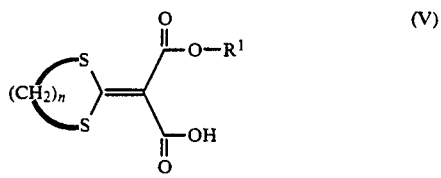 (V)

wherein R¹ and n are the same as defined previously. This reaction can be conducted in the presence of a solvent such as methylene chloride or acetonitrile at a temperature from 0° C. to −15° C.

In another alternative process, the compounds of formula (I) can be prepared by reacting the compounds of formula (VI) with the compounds of formula (VII).

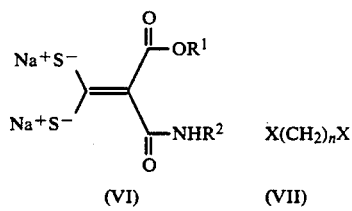

(VI)   (VII)

wherein R¹, R² and n are the same as defined previously; and X is a halogen.

The compound of formula (VI) can be obtained by the reaction of carbon disulfide with the compound of formula (VIII) in the presence of sodium hydroxide at 15°-50° C. in an organic solvent, e.g. N,N-dimethylformamide or acetone,

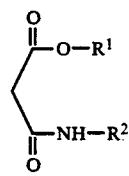 (VIII)

wherein R¹ and R² are the same as defined previously.

In order to obtain the objective compounds of formula (I), the acid chloride of formula (II) and the active ester of formula (IV) are used as an intermediate in the present invention. These intermediates are novel ones, and also constitute the present invention. These intermediates may be made by the processes described below.

Acid anhydrides of formula (II), isolated in a stable form, may be prepared by reacting the monoacid of formula (V) with the acid chloride of R³COOH, wherein R³ is the same as defined previously, in the presence of an organic base, e.g. triethyl amine or pyridine, at 0°-30° C.

The active ester of formula (IV) can be prepared by reacting the monoacid of formula (V) with 1-hydroxybenzotriazole, N-hydroxysuccinimide or N-hydroxyphthalimide in the presence of a dehydrating agent such as N, N'-dicyclohexylcarbodiimide.

The monoacid of formula (V) can be prepared by hydrolyzing one ester group of formula (IX) using the corresponding alcohol as a solvent at ambient temperature;

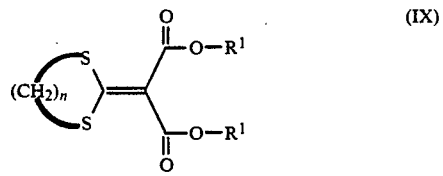 (IX)

wherein R¹ and n are the same as defined previously.

The starting material of formula (VIII) may be prepared by the reaction of alkyl malonyl chloride with the corresponding amine of formula (III).

The compounds of formula (IX) can be prepared by similar methods described in the aforementioned literatures.

In order to make the present invention more fully understood, the following Experiments and Examples are given.

The descriptions of experiments explain the protective and therapeutic effects of the compounds.

Examples are provided to illustrate the preparation of the compounds of formula (I), the starting materials and the related intermediates.

EXAMPLE 1

Isopropyl 2-(1,3-dithietan-2-ylidene)-2-carboxyacetate

Diisopropyl 2-(1,3-dithietan-2-yilidene)malonate (10 g) was added to a solution of potassium hydroxide (3.0 g) in isopropyl alcohol (300 ml). The mixture was stirred at room temperature for 12 hrs, after which water (500 ml) was added to dissolve the solid. The aqueous solution was acidified with acetic acid and the solid formed was filtered. The filter cake was purified with methylene chloride to afford the titled compound as a white solid. (6.6 g, 79%).

m. p.: 123°-124° C.

$^1$H—NMR(CDCl$_3$) δ: 12.30(bs,1H), 5.11(m,1H), 4.00(s,2H), 1.27(d,6H).

IR (KBr) cm$^{-1}$: 1712, 1627.

EXAMPLE 2

Ethyl 2-(1,3-dithietan-2-ylidene)-2-carboxyacetate

Diethyl 2-(1,3-dithietan-2-ylidene)malonate was treated with a solution of potassium hydroxide in ethanol. The resultant solid was isolated and purified by the same method as in Example 1 to afford the titled compound as a white solid. (51%).

m. p.: 166°–167° C.
$^1$H—NMR(DMSO—d$_6$) δ: 4.21(q,2H), 4.14(s,2H), 1.08(t,3H).
IR (KBr) cm$^{-1}$: 1701, 1637.

EXAMPLE 3

Sec-butyl 2-(1,3-dithietan-2-ylidene)-2-carboxyacetate

Di-sec-butyl 2-(1,3-dithietan-2-ylidene)malonate was treated with a solution of potassium hydroxide in sec-butanol. The resultant solid was isolated and purified by the same method as in Example 1 to afford the titled compound as a white solid. (41%).

m. p.: 80°–82° C.
$^1$H—NMR(CDCl$_3$) δ: 12.28(bs,1H), 5.04(m,1H), 4.04(s,2H), 1.77(m,2H), 1.28(d,3H), 0.91(t,3H).
IR (KBr) cm$^{-1}$: 1712, 1627.

EXAMPLE 4

Isopropyl 2-(1,3-dithiolan-2-ylidene)-2-carboxyacetate

Diisopropyl 2-(1,3-dithiolan-2-ylidene)malonate was treated with a solution of potassium hydroxide in isopropyl alcohol. The resultant solid was isolated and purified by the same method as in Example 1 to afford the titled compound as a white solid. (64%).

m. p.: 104°–106° C.
$^1$H—NMR(CDCl$_3$) δ: 13.25(bs,1H), 5.22(m,1H), 3.39(s,4H), 1.11(d,6H).
IR (KBr) cm$^{-1}$: 1711, 1606.

EXAMPLE 5

Isopropyl 2-(1,3-dithietan-2-ylidene)-2-(ethoxycarboxycarbonyl)acetate

Triethylamine (5.18 g) was added to a solution of isopropyl 2-(1,3-dithietan-2-ylidene)-2-carboxyacetate (10 g) in methylene chloride (100 ml). The mixture was cooled to 0° C., to which ethyl chloroformate (5.60 g) was added dropwise and then stirred for an hour. The precipitate was removed by filtration. The filtrate was washed with water, dried and evaporated to afford the titled compound as a pale yellow oil. (10 g, 81%).

$^1$H—NMR(CDCl$_3$) δ: 5.06(m,1H), 4.25(q,2H), 4.05(s,2H), 1.20(t,3H), 1.15(d,6H).
IR (KBr) cm$^{-1}$: 1783, 1706, 1654.

EXAMPLE 6

Ethyl 2-(1,3-dithietan-2-ylidene)-2-(ethoxycarboxycarbonyl)acetate

Following the procedure of Example 5, the titled compound was obtained as a white solid (99%) from ethyl 2-(1,3-dithietan-2-ylidene)-2-carboxyacetate.

m.p.: 38°–39° C.
$^1$H—NMR(CDCl$_3$) δ: 4.25(2q's,4H), 4.05(s,2H), 1.32(2t's,6H).
IR (KBr) cm$^{-1}$: 1767, 1707.

EXAMPLE 7

Sec-butyl 2-(1,3-dithietan-2-ylidene)-2-(ethoxycarboxycarbonyl)acetate

Following the procedure of Example 5, the titled compound was obtained as a yellow oil (97%) from sec-butyl 2-(1,3-dithietan-2-ylidene)-2-carboxyacetate.

$^1$H—NMR(CDCl$_3$) δ: 5.34(m,1H), 4.32(q,2H), 4.08(s,2H), 1.72(m,2H), 1.45(t,3H), 1.34(d,3H), 0.94(t,3H).
IR (KBr) cm$^{-1}$: 1783, 1705, 1652.

EXAMPLE 8

Isopropyl 2-(1,3-dithiolan-2-ylidene)-2-(ethoxycarboxycarbonyl)acetate

Following the procedure of Example 5, the titled compound was obtained as a yellow oil (97%) from isopropyl 2-(1,3-dithiolan-2-ylidene)-2-carboxyacetate.

$^1$H—NMR(CDCl$_3$) δ: 5.13(m,1H), 4.26(q,2H), 3.42(s,4H), 1.72(t,3H), 1.23(d,6H).
IR (KBr) cm$^{-1}$: 1786, 1691.

EXAMPLE 9

Isopropyl 2-(1,3-dithietan-2-ylidene)-2-[(1-benzotriazolyl)oxycarbonyl] acetate

N,N'-Dicyclohexylcarbodiimide (7.1 g) was added to a mixture of isopropyl 2-(1,3-dithietan-2-ylidene)-2-carboxyacetate (10 g) and 1-hydroxybenzotriazole(4.61 g) in methylene chloride(100 ml). The mixture was stirred at room temperature for 4 hrs, after which the precipitate was removed by filtration. The filtrate was concentrated to afford the titled compound as a white solid. (15 g, 96%).

m.p.: 146°–148° C.
$^1$H—NMR(CDCl$_3$) δ: 8.27-7.03(m,4H), 5.18(m,1H), 4.03(s,2H), 1.27(d,6H).
IR (KBr) cm$^{-1}$: 1709, 1655.

EXAMPLE 10

Ethyl 2-(1,3-dithietan-2-ylidene)-2-[(1-benzotriazolyl) oxycarbonyl] acetate

Following the procedure of Example 9, the titled compound was obtained as a white solid (89%) from ethyl 2-(1,3-dithietan-2-ylidene)-2-carboxyacetate.

m.p.: 168°–169° C.
$^1$H—NMR(CDCl$_3$) δ: 8.27-7.06(m,4H), 4.43(q,2H), 4.11(s,2H), 1.37(t,3H).
IR (KBr) cm$^{-1}$: 1728, 1693.

EXAMPLE 11

Sec-butyl 2-(1,3-dithietan-2-ylidene)-2-[(1-benzotriazolyl) oxocarbonyl]acetate

Following the procedure of Example 9, the titled compound was obtained as a white solid (93%) from sec-butyl 2-(1,3-dithietan-2-ylidene)-2-carboxyacetate.

m.p.: 143°–144° C.
$^1$H—NMR(CDCl$_3$) δ: 8.29-7.27(m,4H), 5.02(m,1H), 4.09(s,2H), 1.70(m,2H), 1.31(d,3H), 0.92(t,3H).
IR (KBr) cm$^{-1}$: 1712, 1663.

EXAMPLE 12

Isopropyl 2-(1,3-dithiolan-2-ylidene)-2-[(1-benzotriazolyl)oxycarbonyl] acetate

Following the procedure of Example 9, the titled compound was obtained as a white solid (97%) from isopropyl 2-(1,3-dithietan-2-ylidene)-2-carboxyacetate.

m.p.: 88°–89° C.

$^1$H—NMR(CDCl$_3$) δ: 8.28–7.15(m,4H), 5.24(m,1H), 2.31(s,4H), 1.38(d,6H).

IR (KBr) cm$^{-1}$: 1720, 1687.

EXAMPLE 13

Isopropyl 2-(1,3-dithietan-2-ylidene)-2-carbamoylacetate

A solution of isopropyl 2-(1,3-dithietan-2-ylidene)-2-(ethoxycarboxycarbonyl)acetate (10 g) in methanolic ammonia (60 ml) was stirred at room temperature for 4 hrs. The mixture was concentrated and purified with n-hexane and ethyl ether to give the titled compound as a white solid. (5.2 g, 68%)

m.p.: 128°–129° C.

$^1$H—NMR(DMSO—d$_6$) δ: 7.68(bs,1H), 7.30(bs,1H), 5.13(m,1H), 4.03(s,2H), 1.37(d,6H).

IR (KBr) cm$^{-1}$: 1675, 1647.

EXAMPLE 14

Isopropyl 2-(1,3-dithietan-2-ylidene)-2-(N-ethylcarbamoyl)acetate.

Following the procedure of Example 13, the titled compound was obtained as a white solid (72%) from a solution of isopropyl 2-(1,3-dithietan-2-ylidene)-2-(ethoxycarboxycarbonyl)acetate in methanolic ethylamine.

m.p.: 65°–67° C.

$^1$H—NMR(DMSO—d$_6$) δ: 8.42(bs,1H), 5.25(m,1H), 3.97(s,2H), 3.37(q,2H), 1.29(d,6H), 1.08(t,3H).

IR (KBr) cm$^{-1}$: 1683, 1613.

EXAMPLE 15

Isopropyl 2-(1,3-dithietan-2-ylidene)-2-(N-benzylcarbamoyl)acetate

The mixture of isopropyl 2-(1,3-dithietan-2-ylidene)-2-(ethoxycarboxycarbonyl)acetate (15 g) and benzylamine (6.4 ml) in methylene chloride (150 ml) was stirred at room temperature for 4 hrs. The reaction mixture was then washed with dil-HCl and water to remove benzylamine. The solvent was evaporated and the residue was purified with ethyl acetate to give the titled compound as a white solid. (12.2 g, 77%).

m.p.: 93°–94° C.

$^1$H—NMR(CDCl$_3$) δ: 8.82(bs,1H), 7.52(m,5H), 5.06(m,1H), 4.48(dd,2H), 3.96(s,2H), 1.28(d,6H).

IR (KBr) cm$^{-1}$: 1669, 1615.

EXAMPLE 16

Methyl 2-(1,3-dithietan-2-ylidene)-2-[N-(4-fluorophenyl)carbamoyl]acetate

A mixture of methyl 2-[N-(4-fluorophenyl)carbamoyl]acetate (10 g), carbon disulfide (3.2 ml) and acetone (200 ml) was cooled to 5°–10° C., to which 50% aqueous sodium hydroxide (4.2 ml) was added dropwise. The mixture was stirred at same temperature for 2 hrs, then dibromomethane (4 ml) was added dropwise and the reaction mixture was stirred at room temperature for 1 hr and refluxed for 2 hrs. The solid was removed by filtration and the filtrate was poured onto ice-water. The solid formed was filtered, and dissolved in methylene chloride. The solution was washed with 10% aqueous sodium hydroxide solution and water, then dried. The solvent was evaporated and the residue was purified with ethyl acetate and ethyl ether to give the titled compound as a white solid. (8.5 g, 60%).

m.p.: 141°–142° C.

$^1$H—NMR(CF$_3$COOD) δ: 7.42–7.03(m,4H), 4.15(s,2H), 3.98(s,3H).

IR (KBr) cm$^{-1}$: 1685, 1622.

EXAMPLE 17

Isopropyl 2-(1,3-dithietan-2-ylidene)-2-[N-(4-chlorophenyl)carbamoyl]acetate

A solution of isopropyl 2-(1,3-dithietan-2-ylidene)-2-carboxyacetate (10 g) in methylene chloride (100 ml) was cooled to −10° C. and thereto phosphorous pentachloride (8.9 g) was added portionwise and then stirred for 1 hr. To the reaction mixture pyridine (13.8 ml) and 4-chloroaniline (5.45 g) were added and stirred for 2 hrs. The mixture was washed with dil-HCl, 10% aqueous sodium hydroxide solution and water and then evaporated. The residue was purified with ethyl acetate to afford the titled compound as a white solid. (8.9 g, 61%).

m.p.: 164°–165° C.

$^1$H—NMR(CF$_3$COOD) δ: 7.37(m,4H), 5.21(m,1H), 4.12(s,2H), 1.45(d,6H).

IR (KBr) cm$^{-1}$: 1678.

EXAMPLE 18

Isopropyl 2-(1,3-dithietan-2-ylidene)-2-(N-phenylcarbamoyl)acetate

A solution of isopropyl 2-(1,3-dithietan-2-ylidene)-2-(ethoxycarboxycarbonyl)acetate (10 g) and aniline (3.6 ml) in methylene chloride (100 ml) was stirred at room temperature for 8 hrs. The reaction mixture was washed with 10% aqueous sodium hydroxide solution, dil-HCl and water and then evaporated to dryness. The residue solid was purified with ethyl acetate to give the titled compound as a white solid. (7.9 g, 78%).

m.p.: 115°–116° C.

$^1$H—NMR(CDCl$_3$): 10.52(bs,1H), 7.85–6.75(m,5H), 5.16(m,1H), 3.99(s,2H), 1.34(s,6H).

IR (KBr) cm$^{-1}$: 1671.

EXAMPLE 19

Isopropyl 2-(1,3-dithietan-2-ylidene)-2-[N-(4-trifluoromethylphenyl)carbamoyl]acetate Following the procedure of Example 18, the titled compound was prepared as a white solid (67%) from isopropyl 2-(1,3-dithietan-2-ylidene)-2-(ethoxycarboxycarbonyl)acetate and 4-aminobenzotrifluoride.

m. p.: 151°–152° C.

$^1$H—NMR(CDCl$_3$) δ: 10.78(bs,1H), 7.68(m,4H), 5.40(m,1H), 4.02(s,2H), 1.34(d,6H).

IR (KBr) cm$^{-1}$: 1686, 1623.

EXAMPLE 20

Isopropyl 2-(1,3-dithietan-2-ylidene)-2-[N-(4-hydroxyphenyl)carbamoyl]acetate

Following the procedure of Example 18, the titled compound was prepared as a white solid (66%) from isopropyl 2-(1,3-dithietan-2-ylidene)-2-(ethoxycarboxycarbonyl)acetate and p-aminophenol.

m. p.: 175°-176° C.

$^1$H—NMR(DMSO—$d_6$) δ: 10.20(s,1H), 9.15(s,1H), 7.40-6.73(dd,4H), 5.13(m,1H), 4.21(s,2H), 1.42(d,6H).

IR (KBr) cm$^{-1}$: 1675, 1606.

EXAMPLE 21

Isopropyl 2-(1,3-dithiolan-2-ylidene)-2-[N-(4-trifluoromethylphenyl)carbamoyl]acetate Following the procedure of Example 18, the titled compound was obtained as a white solid (80%) from isopropyl 2-(1,3-dithiolan-2-ylidene)-2-(ethoxycarboxycarbonyl)acetate and 4-aminobenzotrifluoride.

m. p. 139°-140° C.

$^1$H—NMR(CDCl$_3$) δ: 10.90(bs,1H), 7.82-7.65(dd,4H), 5.24(m,1H), 3.40(s,4H), 1.42(d,2H).

IR (KBr) cm$^{-1}$: 1679, 1631.

EXAMPLE 22

Isopropyl 2-(1,3-dithietan-2-ylidene)-2-[N-(2-thiazolyl)carbamoyl]acetate

The solution of isopropyl 2-(1,3-dithietan-2-ylidene)-2-(ethoxycarboxycarbonyl)acetate (10 g) and 2-aminothiazole (4.0 g) in methylene chloride (100 ml) was stirred at room temperature for 24 hrs. The reaction mixture was washed with 10% aqueous sodium hydroxide solution and water and then evaporated. The residue was chromatographed on silica gel column using methylene chloride as an eluent to afford the titled compound as a white solid (6.5 g, 63%).

m. p.: 174°-175° C.

$^1$H—NMR(CDCl$_3$/DMSO—$d_6$) δ: 11.70(bs,1H), 7.24(dd,2H), 5.29(m,1H), 4.19(s,2H), 1.29(d,6H).

IR (KBr) cm$^{-1}$: 1675, 1621.

EXAMPLE 23

Ethyl 2-(1,3-dithietan-2-ylidene)-2-[N-(4-methyl-2-thiazolyl)carbamoyl]acetate

Following the procedure of Example 22, the titled compound was obtained as a white solid (39%) from ethyl 2-(1,3-dithietan-2-ylidene)-2-(ethoxycarboxycarbonyl)acetate and 2-amino-4-methylthiazole.

m. p.: 218°-219° C.

$^1$H—NMR(CDCl$_3$) δ: 11.50(bs,1H), 6.45(s,1H), 4.39(q,2H), 4.02(s,2H), 2.34(s,3H), 1.33(t,3H).

IR (KBr) cm$^{-1}$: 1685.

EXAMPLE 24

Isopropyl 2-(1,3-dithietan-2-ylidene)-2-[N-(4-methyl-2-thiazolyl)carbamoyl]acetate Following the procedure of Example 22, the titled compound was obtained as a white solid (46%) from isopropyl 2-(1,3-dithietan-2-ylidene)-2-(ethoxycarboxycarbonyl)acetate and 2-amino-4-methylthiazole.

m. p.: 197°-198° C.

$^1$H—NMR(CDCl$_3$) δ: 11.62(bs,1H), 6.44(2,1H), 5.16(m,1H), 4.06(s,2H), 2.35(s,3H), 1.43(d,6H).

IR (KBr) cm$^{-1}$: 1678, 1627.

EXAMPLE 25

Sec-butyl 2-(1,3-dithietan-2-ylidene)-2-[N-(4-methyl-2-thiazolyl)carbamoyl]acetate Following the procedure of Example 22, the titled compound was prepared as a white solid (67%) from sec-butyl 2-(1,3-dithietan-2-ylidene)-2-(ethoxycarboxycarbonyl)acetate and 2-amino-4-methylthiazole.

m.p.: 153°-154° C.

$^1$H—NMR(DMSO—$d_6$) δ: 11.67(bs,1H), 6.47(s,1H), 5.01(m,1H), 4.07(s,2H), 2.35(s,3H), 1.49(m,2H), 1.29(d,3H), 0.93(t,3H),

IR (KBr) cm$^{-1}$: 1675, 1624,

EXAMPLE 26

Isopropyl 2-(1,3-dithiolan-2-ylidene)-2-[N-(4-methyl-2-thiazolyl)carbamoyl]acetate Following the procedure of Example 22, the titled compound was prepared as a white solid (41%) from isopropyl 2-(1,3-dithiolan-2-ylidene)-2-(ethoxycarboxycarbonyl)acetate and 2-amino-4-methylthiazole.

m.p.: 161°-162° C.

$^1$H—NMR(CDCl$_3$) δ: 11.85(bs,1H), 6.64(s,1H), 5.24(m,1H), 3.37(s,4H), 2.34(s,3H), 1.42(d,6H),

IR (KBr) cm$^{-1}$: 1668, 1623.

EXAMPLE 27

Isopropyl 2-(1,3-dithietan-2-ylidene)-2-[N-(4-phenyl-2-thiazolyl)carbamoyl]acetate A solution of isopropyl 2-(1,3-dithietan-2-ylidene)-2-(ethoxycarboxycarbonyl)acetate (10 g) and 2-amino-4-phenylthiazole (6.2 g) in N,N-dimethylformamide (100 ml) was stirred at 60° C. for 24 hrs. The reaction mixture was poured onto ice-water (500 ml) and the solid formed was filtered.

The filter cake was dissolved in methylene chloride, and the solution was washed with 10% aqueous sodium hydroxide solution and water and then evaporated to dryness. The residue was chromatographed on silica gel column using methylene chloride as an eluent to afford the titled compound as a white solid. (6.9 g, 54%).

m.p.: 225°-226° C.

$^1$H—NMR(CF$_3$ COOD) δ: 7.99-7.44(m,5H), 7.26(s,1H), 5.25(m,1H), 4.30(s,2H), 1.44(d,6H).

IR (KBr) cm$^{-1}$: 1673.

EXAMPLE 28

Isopropyl 2-(1,3-dithietan-2-ylidene)-2-[N-(1,3,4-thiadiazol-2-yl)carbamoyl]acetate Following the procedure of Example 27, the titled compound (38%) was obtained from isopropyl 2-(1,3-dithietan-2-ylidene)-2-(ethoxycarboxycarbonyl)acetate and 2-amino-1,3,4-thiadiazole.

m.p.: 212°-213° C.

$^1$H—NMR(DMSO—$d_6$) δ: 9.16(s,1H), 5.20(m,1H), 4.26(s,2H), 1.33(d,6H),

IR (KBr) cm$^{-1}$: 1676, 1625.

EXAMPLE 29

Isopropyl 2-(1,3-dithietan-2-ylidene)-2-[N-(2-pyridyl)carbamoyl]acetate

Following the procedure of Example 27, the titled compound (77%) was obtained from isopropyl 2-(1,3-dithietan-2-ylidene)-2-[(1-benzotriazolyl)oxycarbonyl]acetate and 2-aminopyridine.

m.p.: 162°–163° C.

$^1$H—NMR(CDCl$_3$) δ: 11.10(s,1H), 8.72–6.93(m,4H), 5.21(m,1H), 3.99(s,2H), 1.37(d,6H),

IR (KBr) cm$^{-1}$: 1676, 1631,

EXAMPLE 30

Ethyl 2-(1,3-dithietan-2-ylidene)-2-[N-(2-pyridyl)carbamoyl]acetate

Following the procedure of Example 27, the titled compound (51%) was prepared from ethyl 2-(1,3-dithietan-2-ylidene)-2-[(1-benzotriazolyl)oxycarbonyl]acetate and 2-aminopyridine.

m.p.: 181°–183° C.

$^1$H—NMR(CDCl$_3$) δ: 10.97(bs,1H), 8.52–6.72(m,4H), 4.40(q,2H), 4.01(s,2H), 1.34(t,3H),

IR (KBr) cm$^{-1}$: 1676, 1628,

EXAMPLE 31

Sec-butyl 2-(1,3-dithietan-2-ylidene)-2-[N-(2-pyridyl)carbamoyl]acetate

Following the procedure of Example 27, the titled compound (76%) was obtained from sec-butyl 2-(1,3-dithietan-2-ylidene)-2-[(1-benzotriazolyl) oxycarbonyl]acetate and 2-aminopyridine.

m.p.: 118°–119° C.

$^1$H—NMR(CDCl$_3$) δ: 11.03(bs,1H), 8.53–6.74(m,4H), 5.02(m,1H), 4.05(s,2H), 1.51(m,2H), 1.31(d,3H), 0.95(t,3H),

IR (KBr) cm$^{-1}$: 1671, 1632.

EXAMPLE 32

Isopropyl 2-(1,3-dithiolan-2-ylidene)-2-[N-(2-pyridyl)carbamoyl]acetate

Following the procedure of Example 27, the titled compound was obtained as a white solid (53%) from isopropyl 2-(1,3-dithiolan-2-ylidene)-2-[(1-benzotriazolyl)oxycarbonyl]acetate and 2-aminopyridine.

m.p.: 121°–122° C.

$^1$H—NMR(DMSO—d$_6$) δ: 10.61(bs,1H), 8.59–6.79(m,4H), 5.02(m,1H), 3.37(bs,4H), 1.22(d,6H),

IR (KBr) cm$^{-1}$: 1666, 1629,

EXPERIMENT 1

Protective Effect Against Acute Hepatic Damage Induced by Carbon Tetrachloride

Principle

Carbon tetrachloride (CCl$_4$) is a well-known hepatotoxic agent, thus widely used to produce experimental animal models for screening the potential drugs acting upon hepatic diseases. In this experiment test compounds were administered to mice prior to treatment with CCl$_4$. 24 Hours after the CCl$_4$ treatment, the animals were sacrificed and serum alanine aminotransferase (ALT) levels were determined. The hepatoprotective effect of a test compound was evaluated by the suppressive action against the increase of serum ALT induced by CCl$_4$.

Method

The experimental animals were divided into the normal, the CCl$_4$ treated and the test compound treated groups. Each group consisted of 8 mice with body weight of 20–25 grams. The test compounds were suspended in 0.2% sodium carboxymethylcellulose (CMC—Na) solution and administered orally at the dose of 50 mg/125 ml/kg body weight. Only the vehicle 0.2% CMC—Na solution, was administered to the normal and to the CCl$_4$ treated group instead of the test compound suspension.

6 Hours after the drug administration, the CCl$_4$ solution in olive oil was administered orally to the CCl$_4$ treated-group and the test compound treated group at the dose of 50 ul/25 ml olive oil/kg body weight. The normal group was administered with olive oil only at the same dose. 24 Hours after the CCl$_4$ administration, blood samples were collected from the orbital sinus of the animals and the sera were monitored using an automatic blood analyzer (Gilford, SBA 300). The hepatoprotective effect of the test compounds was expressed by the suppressive percentage against the increase of serum ALT level induced by CCl$_4$ calculated by the following formula;

Hepatoprotective effect (%) =

$$\frac{ALT \text{ level (CCl}_4 \text{ group)} - ALT \text{ level (test group)}}{ALT \text{ level (CCl}_4 \text{ group)} - ALT \text{ level (normal group)}} \times 100$$

Results

The test results are shown in Table I.

TABLE I (Protective effect of test compound against increase of serum ALT activity induced by CCl$_4$)

| Compound | Inhibitory (%) |
|---|---|
| Example 13 | 28 |
| Example 15 | 97 |
| Example 18 | 100 |
| Example 19 | 100 |
| Example 21 | 98 |
| Example 22 | 100 |
| Example 24 | 100 |
| Example 26 | 98 |
| Example 27 | 11 |
| Example 28 | 100 |
| Example 29 | 100 |
| Example 32 | 85 |

EXPERIMENT 2

Determination of 50% Effective Dose (ED$_{50}$) of Test Compounds

Principle

The various doses of test compounds were administered to mice, followed by the treatment with CCl$_4$ after 6 hours. 24 Hours after the CCl$_4$ treatment, the serum ALT level of the animals were determined. The hepatoprotective effect of the test compounds and the doses were plotted to form doseresponse curves, from which the ED$_{50}$ doses of the test compounds were estimated.

Method

The experimental animals were divided into the normal, the CCl$_4$ treated and the test compound treated groups. Each group consisted of 8 mice with body weight of 20-25 grams. The test compounds were suspended in 0.2% CMC—Na solution and administered orally at a dose of 50 mg, 25 mg, 12.5 mg or 6.25 mg/125 ml/kg body weight. Only the vehicle, 0.2% CMC—Na solution, was administered to the normal and to the $CCl_4$ treated group instead of the test compound suspension. 6 Hours later, the $CCl_4$ solution in olive oil was administered orally to the $CCl_4$ treated and the test compound treated groups at the dose of 50 ul/25 ml oilve oil/kg body weight. The norm group was administered olive oil only at the same dose. 24 Hours after the $CCl_4$ administration, blood samples were collected from the orbital sinuses of the animals and the sera were obtained by centrifugation. The serum ALT activities were monitored and the hepatoprotective effect of the test compounds were calculated by the same method as described in experiment 1. The percentages were plotted against the corresponding doses of the test compounds to make dose-response curves, from which the 50% effective dose of test compound was estimated.

Results

The 50% effective doses ($ED_{50}$) of the test compounds are shown in Table II.

TABLE II ($ED_{50}$ of test compound)

| Compound | $ED_{50}$ (mg/kg) |
|---|---|
| Example 13 | >50 |
| Example 15 | 10 |
| Example 18 | 7 |
| Example 19 | 6.25 |
| Example 21 | <50 |
| Example 22 | <6.25 |
| Example 24 | <6.25 |
| Example 26 | <50 |
| Example 27 | >50 |
| Example 28 | <6.25 |
| Example 29 | 10 |
| Example 32 | <50 |

EXPERIMENT 3

Acute Toxicity of Test Compounds

Each test compound was suspended in 0.2% CMC—Na solution in various concentrations to make test suspensions. The test suspensions were administered orally to male ICR mice (10 in each group) at various doses. The number of dead mice was counted for 14 days and the value of median lethal dose ($LD_{50}$, g/kg) was calculated by the Hitchifield-Wilcoxon method.

The results are shown in Table III.

TABLE III ($LD_{50}$ of Test Compound)

| Compound | $ED_{50}$ (mg/kg) |
|---|---|
| Example 13 | <5,000 |
| Example 22 | >5,000 |
| Example 24 | >5,000 |
| Example 28 | >5,000 |
| Example 29 | >5,000 |

What is claimed is:

1. A compound of formula (I):

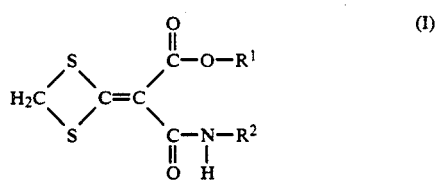

in which $R^1$ is a straight or branched alkyl group having 1 to 5 carbon atoms, and $R^2$ is 4-hydroxyphenyl, halogenophenyl, 4-trifluoromethylphenyl, 2-thiazolyl, 4-methyl-2-thiazolyl, 4-phenyl-2-thiazolyl, 2-pyridyl or 1, 3, 4-thiadiazol-2-yl.

2. The compound of claim 1 in which $R^1$ is methyl, ethyl, isopropyl or sec-butyl, and $R^2$ is 4-hydroxyphenyl, fluorophenyl, chlorophenyl or 4-trifluoromethylphenyl.

3. The compound of claim 1 in which $R^1$ is methyl, ethyl, isopropyl or sec-butyl, and $R^2$ is 2-thiazolyl, 4-methyl-2-thiazolyl or 4-phenyl-2-thiazolyl.

4. The compound of claim 1 in which $R^1$ is methyl, ethyl, isopropyl or sec-butyl, and $R^2$ is 1, 3, 4-thiadiazol-2-yl.

* * * * *

UNITED STATES PATENT AND TRADEMARK OFFICE
CERTIFICATE OF CORRECTION

PATENT NO. : 5,103,013
DATED : April 7, 1992
INVENTOR(S) : Kim et al.

It is certified that error appears in the above-identified patent and that said Letters Patent is hereby corrected as shown below:

ON THE TITLE PAGE
In the Abstract, item [57]:

Line 1, delete "subsittuted" and insert --substituted--.

Signed and Sealed this

Tenth Day of August, 1993

Attest:

MICHAEL K. KIRK

Attesting Officer   Acting Commissioner of Patents and Trademarks